(12) United States Patent
Benz et al.

(10) Patent No.: US 11,011,273 B2
(45) Date of Patent: *May 18, 2021

(54) PATHWAY ANALYSIS FOR IDENTIFICATION OF DIAGNOSTIC TESTS

(71) Applicant: Nantomics, LLC, Culver City, CA (US)

(72) Inventors: Stephen Charles Benz, Santa Cruz, CA (US); Shahrooz Rabizadeh, Los Angeles, CA (US); Christopher Szeto, Soquel, CA (US); Paul Weingarten, Anaheim, CA (US); Chunlin Tao, Newport Coast, CA (US)

(73) Assignee: NantOmics, LLC, Culver City, CA (US)

( * ) Notice: Subject to any disclaimer, the term of this patent is extended or adjusted under 35 U.S.C. 154(b) by 725 days.

This patent is subject to a terminal disclaimer.

(21) Appl. No.: 14/320,214

(22) Filed: Jun. 30, 2014

(65) Prior Publication Data

US 2015/0006445 A1    Jan. 1, 2015

Related U.S. Application Data

(60) Provisional application No. 61/840,669, filed on Jun. 28, 2013.

(51) Int. Cl.
| | | |
|---|---|---|
| *G16H 50/20* | (2018.01) | |
| *C07D 403/14* | (2006.01) | |
| *C07D 403/12* | (2006.01) | |
| *A61P 35/00* | (2006.01) | |
| *A61K 31/506* | (2006.01) | |
| *C07D 401/14* | (2006.01) | |
| *C07D 417/14* | (2006.01) | |
| *C07D 413/14* | (2006.01) | |

(52) U.S. Cl.
CPC ........... *G16H 50/20* (2018.01); *A61K 31/506* (2013.01); *A61P 35/00* (2018.01); *C07D 401/14* (2013.01); *C07D 403/12* (2013.01); *C07D 403/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 9,458,137 B2 * | 10/2016 | Tao ...................... | A61K 31/506 |
| 2003/0124548 A1 | 7/2003 | Hatzis et al. | |
| 2003/0130798 A1 * | 7/2003 | Hood ...................... | G06F 19/12 |
| | | | 702/19 |
| 2003/0154003 A1 | 8/2003 | Eker et al. | |
| 2004/0005621 A1 | 1/2004 | Danenberg | |
| 2004/0088116 A1 * | 5/2004 | Khalil ..................... | G06F 19/12 |
| | | | 702/20 |
| 2005/0043593 A9 * | 2/2005 | Hitt ......................... | G06F 19/24 |
| | | | 600/300 |
| 2005/0064455 A1 * | 3/2005 | Baker ..................... | C12Q 1/6886 |
| | | | 435/6.14 |
| 2005/0165594 A1 * | 7/2005 | Chandra ................. | G06F 19/12 |
| | | | 703/11 |
| 2005/0273305 A1 * | 12/2005 | Thalhammer-Reyero .................... | |
| | | | G05B 17/02 |
| | | | 703/11 |
| 2007/0172844 A1 * | 7/2007 | Lancaster ............ | C12Q 1/6886 |
| | | | 435/6.12 |
| 2008/0275652 A1 * | 11/2008 | Sotiriou ................ | G01N 33/574 |
| | | | 702/20 |
| 2009/0093969 A1 * | 4/2009 | Ladd ....................... | G06F 19/12 |
| | | | 702/19 |
| 2009/0233279 A1 * | 9/2009 | Glinskii ................ | C12Q 1/6886 |
| | | | 435/6.14 |
| 2010/0273711 A1 * | 10/2010 | Potti ..................... | C12Q 1/6886 |
| | | | 514/15.2 |

(Continued)

FOREIGN PATENT DOCUMENTS

| | | |
|---|---|---|
| AU | 2016273897 A1 | 1/2017 |
| CA | 2 919 768 A1 | 12/2014 |

(Continued)

OTHER PUBLICATIONS

Dan, S. et al. An integrated database of chemosensitivity to 55 anticancer drugs and gene expression profiles of 39 human cancer cell lines. Cancer Research 62, 1139-1147 (2002).*

Györffy, B. et al. Gene expression profiling of 30 cancer cell lines predicts resistance towards 11 anticancer drugs at clinically achieved concentrations. International Journal of Cancer 118, 1699-1712 (2006).*

Hess, K. R. et al. Pharmacogenomic predictor of sensitivity to preoperative chemotherapy with paclitaxel and fluorouracil, doxorubicin, and cyclophosphamide in breast cancer. Journal of Clinical Oncology 24, 4236-4244 (2006).*

Huang, F. et al. Identification of candidate molecular markers predicting sensitivity in solid tumors to dasatinib: Rationale for patient selection. Cancer Research 67, 2226-2238 (2007).*

(Continued)

*Primary Examiner* — Soren Harward
(74) *Attorney, Agent, or Firm* — Martin Fessenmaier; Umberg Zipser LLP

(57) ABSTRACT

The present inventive subject matter provides apparatus, systems, and methods in which a diagnostic test is identified, where the diagnostic test is for determining whether a particular treatment is effective for a particular patient based on one or more characteristics of a patient's cells. When a treatment is developed with the potential to treat one or more diseases, the drug can have different effects on different cell lines related to the diseases. A machine learning system is programmed to infer a measurable cell characteristic, out of many different measurable cell characteristics, that has a desirable correlation with the sensitivity data of different cell lines to a treatment. The machine learning system is programmed to then determine, based on the correlation, a threshold level of the cell characteristic the patient should exhibit in order to recommend administering the treatment.

12 Claims, 6 Drawing Sheets

(56) References Cited

U.S. PATENT DOCUMENTS

| | | | |
|---|---|---|---|
| 2010/0304989 A1* | 12/2010 | Von Hoff | C12Q 1/6874 506/9 |
| 2011/0257893 A1* | 10/2011 | Taylor | G01N 33/68 702/19 |
| 2012/0030162 A1* | 2/2012 | Thomson | G06F 19/12 706/52 |
| 2012/0041683 A1 | 2/2012 | Vaske et al. | |
| 2012/0158391 A1* | 6/2012 | Vaske | G06F 19/12 703/11 |
| 2012/0196321 A1 | 8/2012 | Famili et al. | |
| 2013/0144887 A1 | 6/2013 | Chen et al. | |

FOREIGN PATENT DOCUMENTS

| | | | |
|---|---|---|---|
| CN | 1636069 A | | 7/2005 |
| CN | 102985927 A | | 3/2013 |
| CN | 105706097 A | | 6/2016 |
| CN | 110444289 A | | 11/2019 |
| EP | 2 549 399 A1 | | 1/2013 |
| JP | 2004521407 | | 7/2004 |
| JP | 2004524604 | | 8/2004 |
| JP | 2005500832 | | 1/2005 |
| JP | 2010-165230 A | | 7/2010 |
| JP | 2016-528565 A | | 9/2016 |
| JP | 6054555 B2 | | 12/2016 |
| JP | 2017097884 A | | 6/2017 |
| JP | 6388901 B2 | | 9/2018 |
| JP | 2019023871 A | | 2/2019 |
| KR | 10-2013-0105296 A | | 9/2013 |
| KR | 10-2014-0046464 A | | 4/2014 |
| KR | 10-2016-0084363 A | | 7/2016 |
| WO | 02/44423 A2 | | 6/2002 |
| WO | WO 02/44423 A2 * | 6/2002 | C12Q 1/6886 |
| WO | 02/061128 A2 | | 8/2002 |
| WO | 2009/102957 A2 | | 8/2009 |
| WO | 2011/139345 A2 | | 11/2011 |
| WO | 2011-139345 A2 | | 11/2011 |
| WO | 2011/139345 A3 | | 11/2011 |
| WO | 2013-011479 A2 | | 1/2013 |
| WO | 2013-062505 A1 | | 5/2013 |
| WO | 2013/062505 A1 | | 5/2013 |
| WO | 2013150420 A2 | | 10/2013 |
| WO | 2014/059036 A1 | | 4/2014 |
| WO | 2014/071378 A1 | | 5/2014 |
| WO | 2014/210611 A1 | | 12/2014 |
| WO | 2014193982 A1 | | 12/2014 |

OTHER PUBLICATIONS

Jerhammar, F. et al. Fibronectin 1 is a potential biomarker for radioresistance in head and neck squamous cell carcinoma. Cancer Biology & Therapy 10, 1244-1251 (2010).*

Vaske, C. J. et al. Inference of patient-specific pathway activities from multi-dimensional cancer genomics data using PARADIGM. Bioinformatics 26, 237-245 (2010).*

Dudoit, S., Fridlyand, J., Speed, T. P. & Terence, P. Comparison of Discrimination Methods for the Classification of Tumors Using Gene Expression Data. Journal of the American Statistical Association 97, 77-87 (2002).*

Jansen, M. P. H. M. et al. Molecular classification of tamoxifen-resistant breast carcinomas by gene expression profiling. Journal of Clinical Oncology 23, 732-740 (2005).*

Pepe, M. S., Longton, G., Anderson, G. L. & Schummer, M. Selecting differentially expressed genes from microarray experiments. Biometrics 59, 133-142 (2003).*

Su, Y., Murali, T. M., Pavlovic, V., Schaffer, M. & Kasif, S. RankGene: identification of diagnostic genes based on expression data. Bioinformatics 19, 1578-1579 (2003).*

ISA/KR, International Search Report and Written Opinion, Int'l Appln No. PCT/US2014/044950, dated Oct. 30, 2014 (13 pages).

Dudoit, Sandrine, et al. "Comparison of Discrimination Methods for the Classification of Tumors Using Gene Expression Data." Journal of the American Statistical Association, vol. 97, No. 457, 2002, pp. 77-87.

Gyorffy, Balazs, et al. "Gene Expression Profiling of 30 Cancer Cell Lines Predicts Resistance towards 11 Anticancer Drugs at Clinically Achieved Concentrations." International Journal of Cancer, vol. 118, No. 7, 2006, pp. 1699-1712.

Hess, Kenneth R., et al. "Pharmacogenomic Predictor of Sensitivity to Preoperative Chemotherapy With Paclitaxel and Fluorouracil, Doxorubicin, and Cyclophosphamide in Breast Cancer." Journal of Clinical Oncology, vol. 24, No. 26, 2006, pp. 4236-4244.

Huang, F., et al. "Identification of Candidate Molecular Markers Predicting Sensitivity in Solid Tumors to Dasatinib: Rationale for Patient Selection." Cancer Research, vol. 67, No. 5, 2007, pp. 2226-2238.

Jansen, Maurice P.h.m., et al. "Molecular Classification of Tamoxifen-Resistant Breast Carcinomas by Gene Expression Profiling." Journal of Clinical Oncology, vol. 23, No. 4, 2005, pp. 732-740.

Jerhammar, Fredrik, et al. "Fibronectin 1 Is a Potential Biomarker for Radioresistance in Head and Neck Squamous Cell Carcinoma." Cancer Biology & Therapy, vol. 10, No. 12, 2010, pp. 1244-1251.

Su, Y., et al. "RankGene: Identification of Diagnostic Genes Based on Expression Data." Bioinformatics, vol. 19, No. 12, 2003, pp. 1578-1579.

Vaske, Charles J., et al. "Inference of Patient-Specific Pathway Activities from Multi-Dimensional Cancer Genomics Data Using PARADIGM." Bioinformatics, vol. 26, No. 12, 2010, pp. i237-i245.

Dan, Shingo et al. "An Integrated Database of Chemosensitivity to 55 Anticancer Drugs and Gene Expression Profiles of 39 Human Cancer Cell Lines" Cancer Research 62, 1139-1147, Feb. 15, 2002.

Pepe, Margaret Sullivan, et al. "Selecting Differentially Expressed Genes from Microarray Experiments." Biometrics, vol. 59, No. 1, 2003, pp. 133-142.

Ben-Hur, Asa et al. "A User's Guide to Support Vector Machines" Methods in Molecular Biology, 609:223-39, Jan. 2010.

Office Action Received in Japanese Application No. 2018-152970, dated Oct. 8, 2019 (English Translation), 3 pages.

Communication Pursuant to Article 94(3) EPC received for EP Patent Application Serial No. 14816915.4 dated Oct. 21, 2019, 11 pages.

First Examination Report received for Australian Patent Application Serial No. 2014302070 dated Feb. 09, 2016, 03 pages.

Notice of Acceptance received for Australian Patent Application Serial No. 2014302070 dated Aug. 31, 2016, 02 pages.

Second Examination Report received for Australian Patent Application Serial No. 2016273897 dated Jul. 20, 2018, 05 pages.

Third Examination Report received for Australian Patent Application Serial No. 2016273897 dated Oct. 18, 2018, 05 pages.

First Examination Report received for Australian Patent Application Serial No. 2016273897 dated Dec. 18, 2017, 05 pages.

First Office Action received for Canadian Patent Application Serial No. 2919768 dated Mar. 21, 2016, 05 pages.

Second Office Action received for Canadian Patent Application Serial No. 2919768 dated Nov. 18, 2016, 05 pages.

Third Office Action received for Canadian Patent Application Serial No. 2919768 dated Apr. 24, 2017, 05 pages.

Fourth Office Action received for Canadian Patent Application Serial No. 2919768 dated Jan. 2, 2018, 04 pages.

Fifth Office Action received for Canadian Patent Application Serial No. 2919768 dated Sep. 5, 2018, 04 pages.

First Office Action received for Chinese Patent Application Serial No. 201480037201.7 dated Nov. 27, 2017, 76 pages. (Including English Translation).

Decision on Rejection received for Chinese Patent Application Serial No. 201480037201.7 dated Apr. 10, 2019, 53 pages (Including English Translation).

Second Office Action received for Chinese Patent Application Serial No. 201480037201.7 dated Sep. 19, 2018, 50 pages. (Including English Translation).

Extended European Search Report received for European Patent Application Serial No. 14816915.4 dated Feb. 2, 2017, 10 pages.

(56) References Cited

OTHER PUBLICATIONS

Communication Pursuant to Rules 70(2) and 70a(2) EPC received for EP Patent Application Serial No. 14816915.4 dated Feb. 21, 2017, 01 page.
Notice of Reasons for Refusal received for Japanese Patent Application Serial No. 2015563138 dated Jun. 21, 2016, 06 pages. (Including English Translation).
Decision to Grant a Patent received for Japanese Patent Application Serial No. 2015563138 dated Nov. 1, 2016, 05 pages. (Including English Translation).
First Office Action received for Japanese Patent Application Serial No. 2016-232168 dated Mar. 27, 2018, 06 pages (Including English Translation).
Decision to Grant a Patent received for Japanese Patent Application Serial No. 2016232168 dated Jul. 17, 2018, 05 pages (Including English Translation).
Decision to Grant a Patent received for Japanese Patent Application Serial No. 2018152970 dated Feb. 18, 2020, 05 pages (Including English Translation).
International Preliminary Report on Patentability received for PCT Application U.S. Appl. No. PCT/US2014/044950 dated Dec. 29, 2015, 09 pages.
Notice of acceptance received for Australian Patent Application Serial No. 2016273897 dated Dec. 19, 2018, 04 pages.
Carugo et al., "Data Mining Techniques for the Life Sciences", Methods in Molecular Biology, 2010, vol. 609, 408 pages.
Notice of Allowance received for Korean Patent Application Serial No. 1020167002371 dayed Apr. 23, 2020, 4 pages (Including English Translation).
Wang et al., "Identification of aberrant pathways and network activities from high-throughput data", Briefings in Bioinformatics, 2012, vol. 13, No. 4, pp. 406-419.

* cited by examiner

PATHWAY ANALYSIS FOR IDENTIFICATION OF DIAGNOSTIC TESTS

This application claims priority to U.S. Application 61/840,669, filed Jun. 28, 2013. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is pathway analysis, and more particularly pathway analysis using PARADIGM to identify putative diagnostic and/or prognostic markers for treatments of cells or patients with a drug.

BACKGROUND

The following description includes information that may be useful in understanding the present inventive subject matter. It is not an admission that any of the information provided herein is prior art or relevant to the presently claimed inventive subject matter, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Drug discovery is often driven by mechanistic assumptions or screening and refinement of lead compounds in a rationale design manner. While such assumptions and/or screening procedures are often effective with respect to a specific target and a specific drug, effects of the drug on performance and/or regulation of components associated with the target are typically not considered. For example, a kinase inhibitor may be well defined for inhibition of one or more specific kinases, but effects of the inhibitor on other elements or functioning of signaling pathways associated with the kinases are typically not known. Thus, while effectiveness with respects to the mechanism of action may be assessed via a kinase specific test, such tests are often not suitable as diagnostic or prognostic tool as a cell often exhibits compensatory mechanisms to the effect of the drug.

More recently, various improved systems and methods have been described to obtain in silico pathway models of in vivo pathways, and exemplary systems and methods are described in WO 2011/139345 and WO 2013/062505. Further refinement of such models was provided in WO 2014/059036 (collectively referred to herein as "PARADIGM") disclosing methods to help identify cross-correlations among different pathway elements and pathways. While such models provide valuable insights, for example, into interconnectivities of various signaling pathways and flow of signals through various pathways, numerous aspects of using such modeling have not been appreciated or even recognized.

Thus, there is still a need to provide improved systems and methods to identify and/or develop diagnostic and prognostic test, especially for efficacy of a drug.

SUMMARY OF THE INVENTION

The present inventive subject matter provides apparatus, systems, and methods in which a diagnostic test, for determining whether a particular treatment is effective for a particular patient based on one or more characteristics of a patient's cells, is identified. When a drug or other treatment is developed with the potential to treat one or more diseases, the drug can have different effects on different cell lines related to the diseases. For example, one diseased cell line can be extremely sensitive to the drug (e.g., the drug is very effective in inhibiting the disease for this cell line) while another diseased cell line can be extremely resistant to the drug (e.g., the drug is very ineffective in inhibiting the disease for this cell line). The collection of such sensitivity data and other forms of test results can be useful in the diagnosis and/or treatment of conditions, ailments, and diseases. Although information on how each cell line reacts to the drug (the cell line's sensitivity level to the drug) can be gathered fairly easily (e.g., by introducing drugs to different cell lines and measuring their reactions), using a sample cell taken from a patient to suggest its corresponding cell line, and therefore the expected drug effectiveness, remains a challenge.

Therefore, in one aspect of the inventive subject matter, a machine learning system is programmed to infer a measurable cell characteristic, out of many different measurable cell characteristics, that has a desirable correlation with the sensitivity data of different cell lines to a drug or other form of treatment. The machine learning system is programmed to then determine, based on the correlation, a threshold level of the cell characteristic the patient should exhibit in order to recommend administering the drug or other form of treatment.

In some embodiments, the machine learning system is informationally coupled to a pathway model database. The pathway model database stores multiple data sets derived from omics data of multiple distinct diseased cell lines, respectively. Each different data set includes pathway element data corresponding to a different diseased cell line. The machine learning system is programmed to use the pathway model database to generate, for each cell characteristic of the many measurable cell characteristics, data that infers an expression based on the magnitude of the characteristics of the multiple distinct diseased cell lines according to the pathway element data stored in the pathway model database.

After that, the machine learning system is programmed to derive, for each cell expression, a correlation between the inferred magnitudes of the cell expression and the sensitivity data with respect to the multiple distinct diseased cell lines. By comparing these derived correlations, the machine learning system is able to identify a single expression having the most desirable (e.g., the best fit) correlation with sensitivity data with respect to the multiple diseased cell lines. It is contemplated in the inventive subject matter that the machine learning system's comparison of the derived correlations can identify an expression, that can include a single characteristic, a combination of characteristics, or an arrangement of characteristics, having the most desirable correlation with sensitivity data.

In one view of the inventive subject matter, the sensitivity data or other test results can be based on the amount of treatment required to produce a particular result. Treatments include, but are not limited to, the administering of antineoplastic drugs, therapeutic and/or prophylactic pharmaceutical agents, nutraceutical agents, and other compounds, as well as radiation, exercise, fasting, psychotherapy, and other modalities or regimens. The nature of the test results may vary considerably, and can include responsiveness to treatment with a drug (e.g., $GI_{50}$ value, $IC_{50}$ value), systemic effects, induction of apoptosis, local effects, and cellular effects.

The inventive subject matter contemplates the measurable cell characteristics to include enzymatic activity, regulatory activity, metabolic activity, expression activity including transcription, translation, and/or post-translational modification, signaling pathways, and other various cellular pathways, as well as receptors, kinases, regulatory elements, and other cellular complexes or elements. It is generally preferred that the cell characteristic has at least an assumed or known molecular target.

The measurable cell expression that the machine learning system is programmed to infer can be a single characteristic, a combination of characteristics, or an arrangement of characteristics. The machine learning system is programmed to receive sensitivity data of the different cell lines, allowing it to associate an inferred magnitude of a cell characteristic with each cell line. The sensitivity data can be gathered by performing various tests or procedures in a lab or other suitable environment by technicians or machines.

In another aspect, the inventors contemplate a method of determining a marker for treating a disease using a drug based on omics data of distinct diseased cell lines. The method includes a step of informationally coupling a pathway model database to a machine learning system, wherein the pathway model database stores a plurality of distinct data sets derived from omics data of a plurality of distinct diseased cell lines, respectively, and each data set comprises a plurality of pathway element data. The machine learning system receives sensitivity data associated with the plurality of distinct diseased cell lines. The sensitivity data indicates a sensitivity level of each one of the plurality of distinct diseased cell lines reacting to the drug, and can be generated by testing example diseased cells of the plurality of distinct diseased cell lines with the drug.

In a further step, the machine learning system infers an cell characteristic (e.g. one complex or multiple complexes) having a correlation with the sensitivity data with respect to the plurality of distinct diseased cell lines by traversing the plurality of pathway element data corresponding to the plurality of distinct diseased cell lines in the pathway model database. The machine learning system then determines a threshold expression level exhibited by a patient for recommending the drug to treat the disease based on the correlation.

It should be noted that the expression can be defined in various manners. For example, the expression can be defined by at least a concentration of a complex, a combination of multiple complexes, or a ratio of concentration between two or more complexes.

Most typically, the expression is inferred out of possible expressions present in the plurality of distinct diseased cell lines. When inferring the expression for each one of the possible expressions present in the plurality of distinct diseased cell lines, it is contemplated that data points can be generated to indicate magnitudes for each one of the possible expressions present in the plurality of distinct diseased cell lines according to the plurality of pathway element data. The machine learning system can then derive a correlation between the magnitudes for each one of the possible expressions and the sensitivity data with respect to the plurality of distinct diseased cell lines. Thus, it should be appreciated that machine learning can be used to infer the expression having an optimal correlation out of the derived correlations corresponding to the possible expressions.

While not limiting the inventive subject matter, it is generally preferred that output data are generated that comprise a treatment recommendation for the patient. A sample diseased cell can be taken from the patient, and a magnitude of the expression present in the sample diseased cell can be measured so that the treatment recommendation generated is based on the measured magnitude of the expression.

Viewed from a different perspective, it should be appreciated that the plurality of distinct diseased cell lines can differ from one another with respect to sensitivity to the drug. For example, a first set of the plurality of distinct diseased cell lines are sensitive to treatment with the drug, and wherein a second set of the plurality of distinct diseased cell lines are resistant to treatment with the drug.

With respect to omics data, all known omics data are considered suitable, and preferred omics data include gene copy number data, gene mutation data, gene methylation data, gene expression data, RNA splice information data, siRNA data, RNA translation data, and protein activity data. Likewise, numerous data formats are deemed appropriate for use herein, however, particularly preferred data formats are PARADIGM datasets. Pathway element data may vary considerably, however, pathway element data includes an expression state of a gene, a protein level of a protein, and/or a protein activity of a protein.

Viewed from another perspective, the inventors contemplate a system for determining a marker for treating a disease using a drug based on omics data of distinct diseased cell lines. The system includes a pathway model database for storing a plurality of distinct data sets derived from omics data of a plurality of distinct diseased cell lines, respectively, and each data set comprises a plurality of pathway element data. The system further includes a machine learning system informationally coupled to the pathway model database. The machine learning system is programmed to (i) receive sensitivity data associated with the plurality of distinct diseased cell lines, wherein the sensitivity data indicates a sensitivity level of each one of the plurality of distinct diseased cell lines reacting to the drug, (ii) infer an expression having a correlation with the sensitivity data with respect to the plurality of distinct diseased cell lines by traversing the plurality of pathway element data corresponding to the plurality of distinct diseased cell lines in the pathway model database, and (iii) determine a threshold expression level exhibited by a patient for recommending the drug to treat the disease based on the correlation.

As noted above, it is contemplated that the expression is inferred out of possible expressions present in the plurality of distinct diseased cell lines. The machine learning system is programmed to infer the expression for each one of the possible expressions present in the plurality of diseased cell lines by (i) generating data points that indicate magnitudes of the one expression present in the plurality of distinct diseased cell lines according to the plurality of pathway element data, and (ii) deriving a correlation between the magnitudes of the one expression and the sensitivity data with respect to the plurality of distinct diseased cell lines. Additionally, the machine learning system can be further programmed to use machine learning to infer the expression having an optimal correlation out of the derived correlations corresponding to the possible expressions.

Viewed from another perspective, the inventors contemplate a non-transient computer readable medium containing program instructions for causing a computer system comprising a machine learning system to perform a method. The machine learning system is informationally coupled to a pathway model database that stores a plurality of distinct data sets derived from omics data of a plurality of distinct diseased cell lines, respectively, and wherein each data set comprises a plurality of pathway element data. The method comprises the steps of (i) receiving, by the machine learning system, sensitivity data associated with the plurality of distinct diseased cell lines, wherein the sensitivity data indicates a sensitivity level of each one of the plurality of distinct diseased cell lines reacting to the drug, (ii) inferring, by the machine learning system, an expression having a correlation with the sensitivity data with respect to the plurality of distinct diseased cell lines by traversing the plurality of pathway element data corresponding to the plurality of distinct diseased cell lines in the pathway model database, and (iii) determining, by the machine learning system, a threshold expression level exhibited by a patient for recommending the drug to treat the disease based on the correlation.

Most typically, the expression is inferred out of possible expressions present in the plurality of distinct diseased cell lines. Additionally, the step of inferring the expression comprises the steps of (i) generating data points that indicate magnitudes of the one expression present in the plurality of distinct diseased cell lines according to the plurality of pathway element data, and (ii) deriving, by the machine learning system, a correlation between the magnitudes of the one expression and the sensitivity data with respect to the plurality of distinct diseased cell lines. It should be appreciated that the steps of inferring can be performed for each one of the possible expressions present in the plurality of diseased cell lines. Machine learning can then be used to infer the expression having an optimal correlation out of the derived correlations corresponding to the possible expressions.

DETAILED DESCRIPTION

Figure 1:
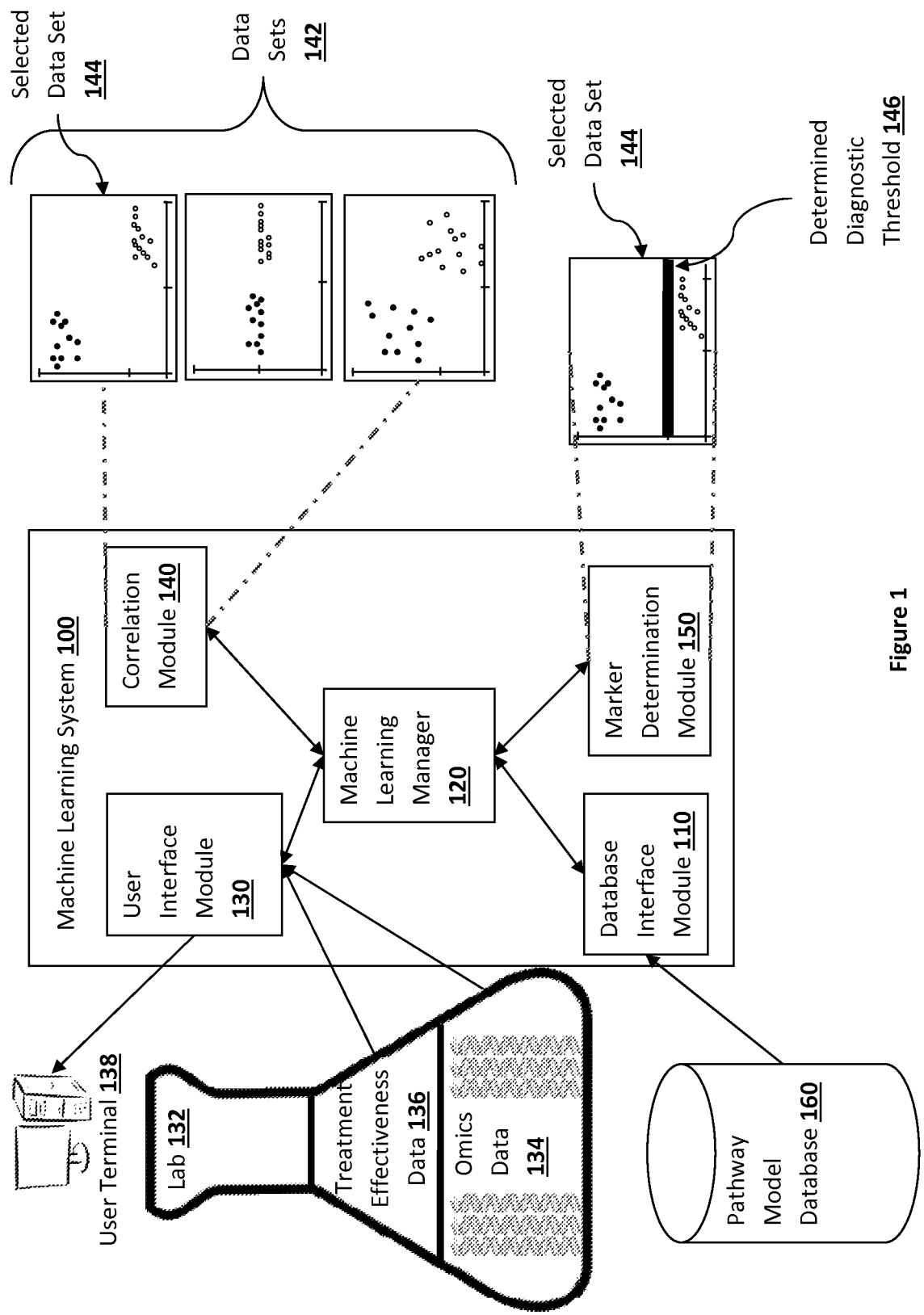
FIG. 1 depicts an example machine learning system of some embodiments.

It should be noted that any language directed to a computer should be read to include any suitable combination of computing devices, including servers, interfaces, systems, databases, agents, peers, engines, modules, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints and open-ended ranges should be interpreted to include only commercially practical values. The recitation of ranges of values herein is merely intended to serve as a shorthand method of referring individually to each separate value falling within the range. Unless otherwise indicated herein, each individual value within a range is incorporated into the specification as if it were individually recited herein.

Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The present inventive subject matter provides apparatus, systems, and methods in which a diagnostic test is identified, where the diagnostic test is for determining whether a particular treatment (e.g., drug, pharmaceutical compound, therapeutic regiment, etc.) is effective for a particular patient based on one or more characteristics of a patient's cells. When a drug or other treatment is developed with the potential to treat one or more diseases, the drug can have different effects on different cell lines related to the diseases. For example, one diseased cell line can be extremely sensitive to the drug (e.g., the drug is very effective in inhibiting the disease for this cell line) while another diseased cell line can be extremely resistant to the drug (e.g., the drug is very ineffective in inhibiting the disease for this cell line). The collection of such sensitivity data and other forms of test results can be useful in the diagnosis and/or treatment of conditions, ailments, and diseases. Although information on how each cell line reacts to the drug (the cell line's sensitivity level to the drug) can be gathered fairly easily (e.g., by introducing drugs to different cell lines and measuring their reactions), using a sample cell taken from a patient to suggest its corresponding cell line, and therefore the expected drug effectiveness, remains a challenge.

Therefore, in one aspect of the inventive subject matter, a machine learning system is programmed to infer a measurable cell characteristic, out of many different measurable cell characteristics present in the cell lines, that has a desirable correlation with the sensitivity data of different cell lines to a drug or other form of treatment. The machine learning system is programmed to then determine, based on the correlation, a threshold level of the cell characteristic the patient should exhibit in order to recommend administering the drug or other form of treatment.

In some embodiments, the machine learning system is informationally coupled to a pathway model database. In some embodiments, the pathway model database includes Pathway Recognition Algorithm Using Data Integration on Genomic Models (PARADIGM) database, which is further described in International Publication WO2011/139345 to Charles J. Vaske et al., filed on Apr. 29, 2011 and International Publication WO 2013/062505 to Charles J. Vaske et al., filed on Oct. 26, 2011.

The pathway model database stores multiple data sets derived from omics data of multiple distinct diseased cell lines, respectively. Each different data set includes pathway element data corresponding to a different diseased cell line. The machine learning system is programmed to use the pathway model database to generate, for each cell expression of the many measurable cell characteristics, data that infers the magnitude of the expressions of the multiple distinct diseased cell lines according to the pathway element data stored in the pathway model database.

After that, the machine learning system is programmed to derive, for each cell characteristic, a correlation between the inferred magnitudes of the cell expression and the sensitivity data with respect to the multiple distinct diseased cell lines. By comparing these derived correlations, the machine learning system is able to identify the single expression having the most desirable (e.g., the best fit) correlation with sensitivity data with respect to the multiple diseased cell lines. In some embodiments, the machine learning system uses machine learning algorithms (e.g., Support Vector Machines (SVM), etc.) to identify the single expression with the most desirable correlation with the sensitivity data. More details about the SVM machine learning algorithm are described in the publication entitled "A User's Guide to Support Vector Machines" by Ben-Hur et al., which is incorporated by reference herein in its entirety. It is contemplated that the single expression can include a single, a combination, or an arrangement of measurable cell characteristics having the most desirable correlation with sensitivity data.

In one view of the inventive subject matter, the sensitivity data or other test results can be based on the amount of treatment required to produce a particular result. Treatments include, but are not limited to, the administering of antineoplastic drugs, therapeutic and/or prophylactic pharmaceutical agents, nutraceutical agents, and other compounds, as well as radiation, exercise, fasting, psychotherapy, and other modalities or regimens. The nature of the test results may vary considerably, and include responsiveness to treatment with a drug (e.g., $GI_{50}$ value, $IC_{50}$ value), systemic effects, local effects, and cellular effects.

The inventive subject matter contemplates the measurable cell characteristics to include enzymatic activity, regulatory activity, metabolic activity, expression activity including transcription, translation, and/or post-translational modification, signaling pathways, and other various cellular pathways, as well as receptors, kinases, regulatory elements, and other cellular complexes or elements. It is generally preferred that the cell characteristic has at least an assumed or known molecular target. In some embodiments, the concentration or other quantitative description of the cell characteristic is used to qualify the characteristic.

The single cell expression the machine learning system is programmed to infer can be a single characteristic, a combination of characteristics, or an arrangement of characteristics. In order to infer a single measurable characteristic, the machine learning system is programmed to first receive sensitivity data of the different cell lines. The sensitivity data can be gathered by performing various tests or procedures in a lab or other suitable environment by technicians or machines.

One should appreciate that the disclosed techniques provide many advantageous technical effects including allowing medical personnel to provide customized treatment to patients based on patients' diseased cell lines.

FIG. 1 illustrates an example machine learning system 100 of some embodiments of the inventive subject matter. Machine learning system 100 comprises database interface module 110, machine learning manager 120, user interface module 130, correlation module 140, and marker determination module 150. Machine learning manager 120 is programmed to send commands to and receive information and/or other data elements from user interface module 130, database interface module 110, correlation module 140, and marker determination module 150. Machine learning manager 120 also acts as a conduit for transferring data elements between modules 110, 130, 140, and 150. Machine learning manager 120 directs the flow of data elements from the interface modules 110 and 130 to the analysis modules 140 and 150, between correlation module 140 and marker determination module 150, and ultimately to user interface module 130 for output to user terminal 138.

User interface module 130 is informationally coupled to an input device (e.g., a computer terminal, etc.) to receive data sets corresponding to each surveyed cell line from lab 132. The data sets received at the user interface module 130 includes treatment effectiveness data 136 and omics data 134. Various procedures, tests, and analysis suitable to generate omics data and treatment effectiveness data are performed on each surveyed cell line by lab 132. As a result, treatment effectiveness data 136 and omics data 134 are derived for each surveyed cell line.

Omics data includes but is not limited to information related to genomics, lipidomics, proteomics, transcriptomics, metabolomics, metabonomics, nutritional genomics, and other characteristics and biological functions of a cell. The surveyed cell lines may include cells from a single or multiple different tissues or anatomical regions, cells from a single or multiple different hosts, as well as any permutation of combinations. Additionally, the surveyed cell lines may be healthy cells, unhealthy cells, or any combination. In a preferred embodiment, the surveyed cell lines comprise neoplastic cells.

In some embodiments of the inventive subject matter, an evaluated treatment may be effective in treating multiple diseases. As such, the surveyed cell lines preferably comprise cells from multiple different tissue and anatomical regions, multiple cells with distinct diseases, conditions, or ailments, or some combination of both.

It is contemplated by the subject matter of the invention that omics data 134 generated by lab 132 comprises sufficient information to assess various characteristics of each surveyed cell line. The cell characteristics include enzymatic activity, regulatory activity, metabolic activity, expression activity including transcription, translation, and/or post-translational modification, signaling pathways, and other various cellular pathways, as well as receptors, kinases, regulatory elements, and other cellular structures, complexes, or elements.

In the embodiment depicted in FIG. 1, the test results related to an evaluated treatment comprise treatment effectiveness data 136. Treatment effectiveness data 136 indicates how effective a treatment is to the different distinct cell lines. In other words, treatment effectiveness data 136 (also known as "sensitivity data") includes data that indicate how sensitive (e.g., on a scale from extremely sensitive to extremely resistant) each cell line is to a particular treatment. The treatments can include drug treatments such as administering of antineoplastic drugs, therapeutic and/or prophylactic pharmaceutical agents, nutraceutical agents, and other compounds, as well as radiation, exercise, fasting, psychotherapy, and other modalities or regimens. Additionally, the evaluated treatment can include any reasonable combination of administering compounds and/or modalities. The nature of the test results may vary considerably, and include responsiveness to treatment with a drug (e.g., $GI_{50}$ value, $IC_{50}$ value), systemic effects, local effects, and cellular effects.

There are many ways to derive and measure treatment effectiveness data 136 for a particular treatment. For example, effectiveness data can be derived by administering the evaluated treatment to each and every diseased cell line, and measure the effect of the evaluated treatment on each diseased cell line. The measurement can be based on an amount of drug needed to obtain a threshold inhibition effect of the disease in the cell line (e.g., the amount of drug needed to reduce the activities of the disease by half).

Figure 2:
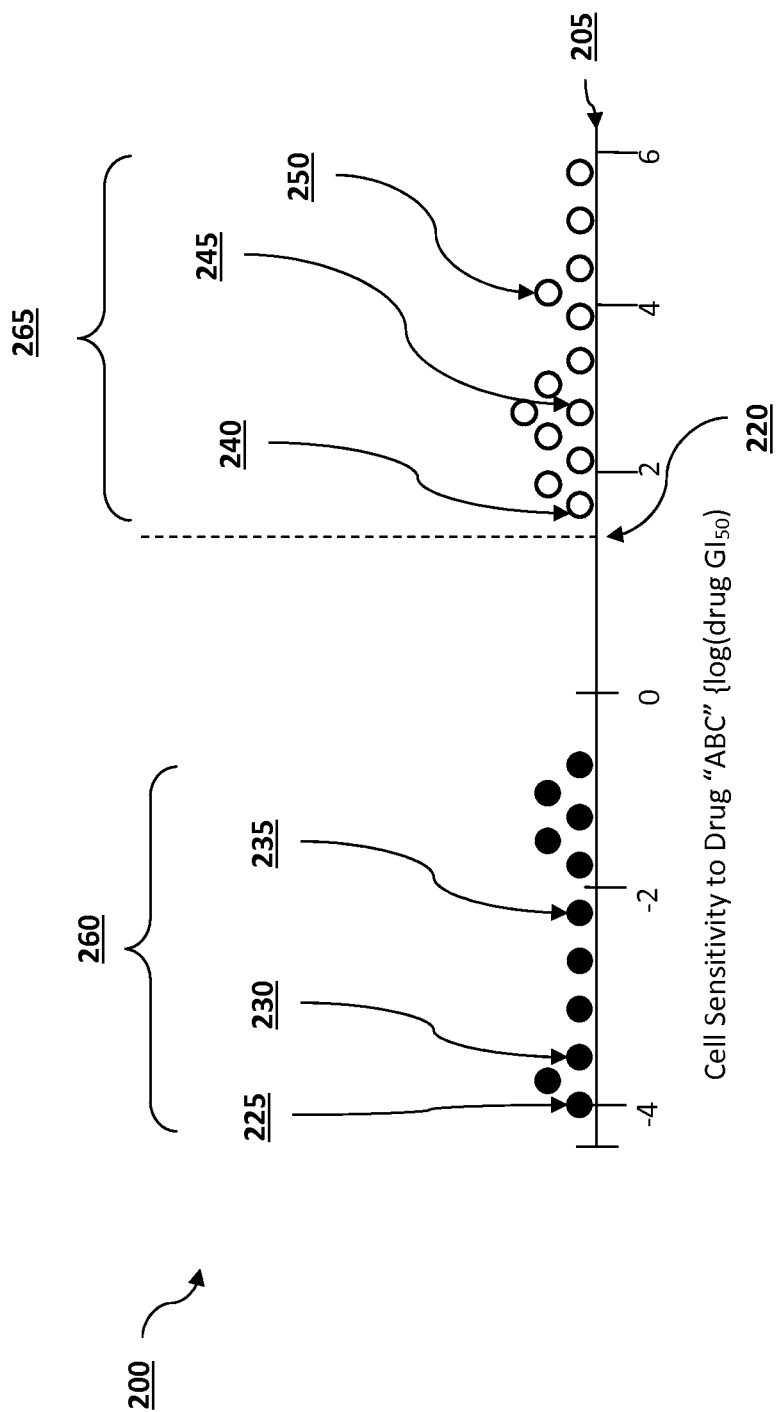
FIG. 2 depicts a graph illustrating different sensitivity levels of the cell lines reacting to a particular treatment along.

FIG. 2 illustrates a graph 200 showing a graphical representation of an example set of treatment effectiveness data 136 that represents how effective NANT3456 is on a set of cell lines. NANT3456 is described in more detail in WO/2014/071378, published May 8, 2014, which is incorporated by reference herein. In some embodiments, the data points on FIG. 2 represent distinct cell lines from different tissues, distinct cell lines from the same tissue, or any combination thereof. Further, the cell lines may be derived from a single host, multiple distinct hosts, or any combination. In this example, NANT3456 is known to be capable of treating diseases associated with the set of cell lines (e.g., cell lines MV411, TT, AN3CA, K562, PC3, HCT116, ASPC1, MDAMB231, TF1, NCIH23, MIAPACA2, HS766T, CAPAN2, A549, HT29, U937, BXPC3, CAPAN1, and SU8686). The various solid circle data points 260 and 265 in graph 200 represent the various cell lines illustrated above. For example, data point 225 can represent cell line MV411, data point 230 can represent cell line TT, data point 235 can represent cell line PC3, data point 240 can represent NCIH23, data point 245 can represent cell line HT29, data point 250 can represent cell line CAPAN1, and so forth.

The only axis (axis 205) of graph 200 indicates a range of possible treatment effectiveness values (e.g., from −4 through 6). In this example, the treatment effectiveness values are expressed in the $\log_{10}$ units of nanomolar drug concentrations for the $GI_{50}$ value for a drug/treatment (e.g., the amount of concentration of the drug to achieve a threshold effectiveness). Thus, a treatment effectiveness value of −4 (far left of the graph 200) indicates that the drug is extremely sensitive to the treatment and a treatment effectiveness value of 6 (far right of the graph 200) indicates that the drug is extremely resistant to the treatment. Thus, as shown in graph 200, cell lines 225, 230, and 235 are more sensitive to NANT3456 than cell lines 240, 245, and 250.

Upon receiving treatment effectiveness data 136 and omics data 134, user interface module 130 is programmed to transfer those data sets to machine learning manager 120. The machine learning manager then sends treatment effectiveness data 136 and omics data 134 to correlation module 140 for generating correlations. In some embodiments, upon receiving treatment effectiveness data 136, correlation module 140 first divides (classifies) the cell lines into two groups (sensitive cell lines and resistant cell lines) based on treatment effective data 136.

Compound 79

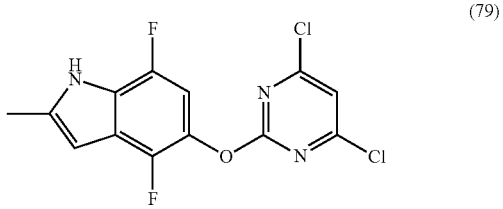

(79)

The solution of 4, 6-dichloro-2-methylsulfonylpyrimidine (3.72 g, 16.38 mmol), and 2-methyl-4,7-di-fluoro-1-H-indol-5-ol (3.00 g, 16.38 mmol) in THF (100 ml) was cooled to −78° C. with dry-ice/acetone. A suspension of potassium t-butoxide (2.30 g, 20.47 mmole) in THF (50 ml) was added to the reaction mixture dropwise. The temperature of the mixture was controlled below −50° C. After addition, the reaction was stirred at −78° C. for 1 h, then warmed up to room temperature over a period of 1 h. The TLC was checked and both starting materials were consumed. Saturated ammonium chloride in water was added and the mixture was extracted with ethyl acetate/hexanes (80/20) three times. The combined organic was washed with brine, dried over sodium sulfate and concentrated. The crude product was applied to silica gel and eluted with 15% ethyl acetate in hexanes. The collected fraction was concentrated to give the desired product as light-yellow solids (79) (4.20 g, 78% yield). The solids were directly used for the next step reaction without further purification.

Compound 86

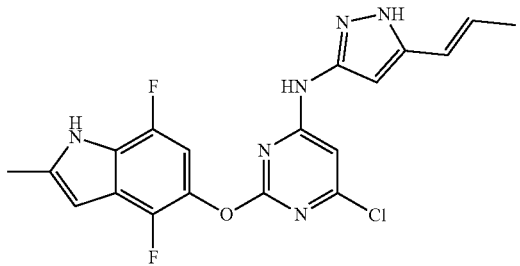

(86)

The solution of compound 79 (4.20 g, 12.72 mmol), (E)-5-(prop-1-en-1-yl)-1H-pyrazol-3-amine (2.82 g, 22.90 mmol), sodium iodide (2.86 g, 19.08 mmol) and DIPEA (3.33 mL, 19.08 mmol) in DMF (35 mL) was stirred at 65° C. for 48 hours. TLC was checked and the starting material was consumed. The mixture was cooled with ice and the solids were collected by filtration, and washed with water & hexanes. The slides were dissolved into dichlomethane/methanol. The solution was concentrated to minimum amount of solvents. The solids were collected by filtration, and washed with methanol to give yellow solids (1.90 g). The mother liquid was purified by column. The desired parts were collected, concentrated, and filtered to give light-yellow solids (0.82 g). The combined solids (86) were used for the next step reactions (2.72 g, 51%) 1H NMR (400 MHz, DMSO-d6) o 12.15 (br, 1H), 11.80 (br, 1H), 10.40 (br, 1H), 6.95 (dd, J=10.8 Hz, J=5.6 Hz, 1H), 6.40 (br, 1H), 6.22 (s, 1H), 5.70-5.10 (m, 3H), 2.40 (s, 3H), 1.78 (br, 3H); ESI-MS: calcd for ($C_{19}H_{15}ClF_2N_6O$) 416, found 417 (MH+).

Alternatively, compound 86 can also be prepared from the reaction of 6-chloro-N-(5propenyl-1H-pyrazol-3-yl)-2-(methylsulfonyl)pyrimidin-4-amine and 2-methyl-4,7-difluro-1-H-indol-5-ol with the same protocol as described earlier.

Compound 87

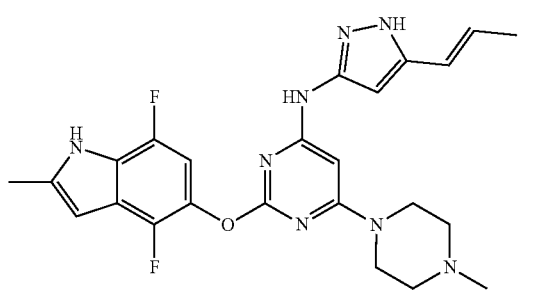

(87)

The solution of compound 86 (45 mg, 0.11 mmol), 1-methylpiperazine (270 mg, 2.70 mmol) and DIPEA (0.10 ml, 0.54 mmol) in iso-propanol (3.0 mL) and acetonitrile (1.0 mL) was stirred at 85° C. for 3 days. TLC was checked and the starting material was consumed. Dilute sodium bicarbonate was added and the mixture was extracted with DCM three times. The combined organic was washed with brine, dried over sodium sulfate, and concentrated. The crude product was purified on column (0.15% methanol in DCM). The collected fraction was concentrated to give the desired product as off-white solids (87) (33 mg, 66% yield). 1H NMR (400 MHz, DMSO-d6) δ 11.90 (br, 1H), 11.71 (br, 1H), 9.30 (br, 1H), 6.85 (dd, J=10.8 Hz, J=5.6 Hz, 1H), 6.29 (s, 1H), 5.80-5.00 (m, 4H), 3.40 (br, 4H), 2.40 (m, 7H), 2.18 (s, 3H), 1.68 (d, J=6.8 Hz, 3H); ESI-MS: calcd for ($C_{24}H_{26}F_2N_8O$) 480, found 481 (MH+).

In some of these embodiments, the correlation module 140 can divide the set of cell lines by identifying a threshold effectiveness value such that cell lines that fall below the threshold effectiveness value (more sensitive or effective than the threshold effectiveness value) are considered to be sensitive cell lines and cell lines that fall above the threshold effectiveness value (less sensitive or effective than the threshold effectiveness value) are considered to be resistant cell lines. The threshold effectiveness value can be generated by taking a median value of all treatment effectiveness values in this treatment effectiveness data set 136. For example, correlation module 140 can generate a threshold effective value to be 1.7 (as indicated by the dotted line 220 of graph 200). Thus, the cell lines represented by data point group 260 (indicated by black circle data points, including cell lines 225, 230, and 235) are considered to be sensitive cell lines and cell lines represented by data point group 265 (indicated by white circle data points, including cell lines 240, 245, and 250) are considered to be resistant cell lines. In some embodiments, the division of cell lines into sensitive and resistant groups enables various machine learning algorithms to infer correlations between omics data 134 and treatment effectiveness data 136. Details about inferring the correlations will be further explained below.

Referring back to FIG. 1, database interface module 110 of machine learning system 100 is informationally coupled with pathway model database 160 to transfer data sets from pathway model database 160 to machine learning system 100. In some embodiments, the pathway model database stores multiple data sets derived from omics data of multiple distinct diseased cell lines, respectively. Each different data set includes pathway element data corresponding to a different diseased cell line. In some embodiments, and as an example, the pathway model database includes Pathway Recognition Algorithm Using Data Integration on Genomic Models (PARADIGM) database, which is further described in International Publication WO2011/139345 to Charles J. Vaske et al., filed on Apr. 29, 2011 and International Publication WO 2013/062505 to Charles J. Vaske et al., filed on Oct. 26, 2011.

In some embodiments, data sets are sent and received between pathway model database 160 and interface module 110, allowing new data to be added to pathway model database 160 by interface module 110.

Correlation module 140 of machine learning system 100 is programmed to analyze and evaluate the correlation between data sets from drug effectiveness data 136 and omics data 134 in combination with data sets from pathway module database 160. Such data sets are depicted as examples at data sets 142. In some embodiments, correlation module 140 is programmed to evaluate the correlation between some or all of the surveyed cell line's drug effectiveness and all possible expressions present in the cell lines. To do this, correlation module 140 first identifies all possible expressions that can be found in the diseased cell lines. The possible expressions can include each and every single characteristic present in the diseased cell lines, and any and all possible permutations of combinations of the characteristics. For example, if characteristics A, B, and C are found in the diseased cell lines, the possible expressions can include characteristic A, characteristic B, characteristic C, combination of characteristics A and B, combination of characteristics A and C, combination of characteristics B and C, and combination of characteristics A, B, and C.

For each diseased cell line, correlation module 140 traverses the pathway element data in the pathway model database 160 to infer magnitudes of the different possible expressions. To perform this inferring step, correlation module 140 of some embodiments takes the omics data 134 for each cell line (that was received via the user interface module 130), traverses the pathway element data within the pathway model database 160 based on the omics data 134, and records the activities from the expressions present in the pathway element data. In some embodiments, the inference of the magnitudes is performed by a computer system such as PARADIGM as mentioned above. Then for each expression from all of the possible expressions identified, correlation module 140 derives a correlation between the expression magnitudes of the cell lines and the treatment effectiveness data of the cell lines. FIGS. 3-6 illustrates different graphs (graphs 300, 400, 500, and 600) that represent correlations between the different expressions and the treatment effectiveness data that are generated by correlation module 140 using inferred expression data from pathway model database 160 and treatment effectiveness data.

Figure 3:
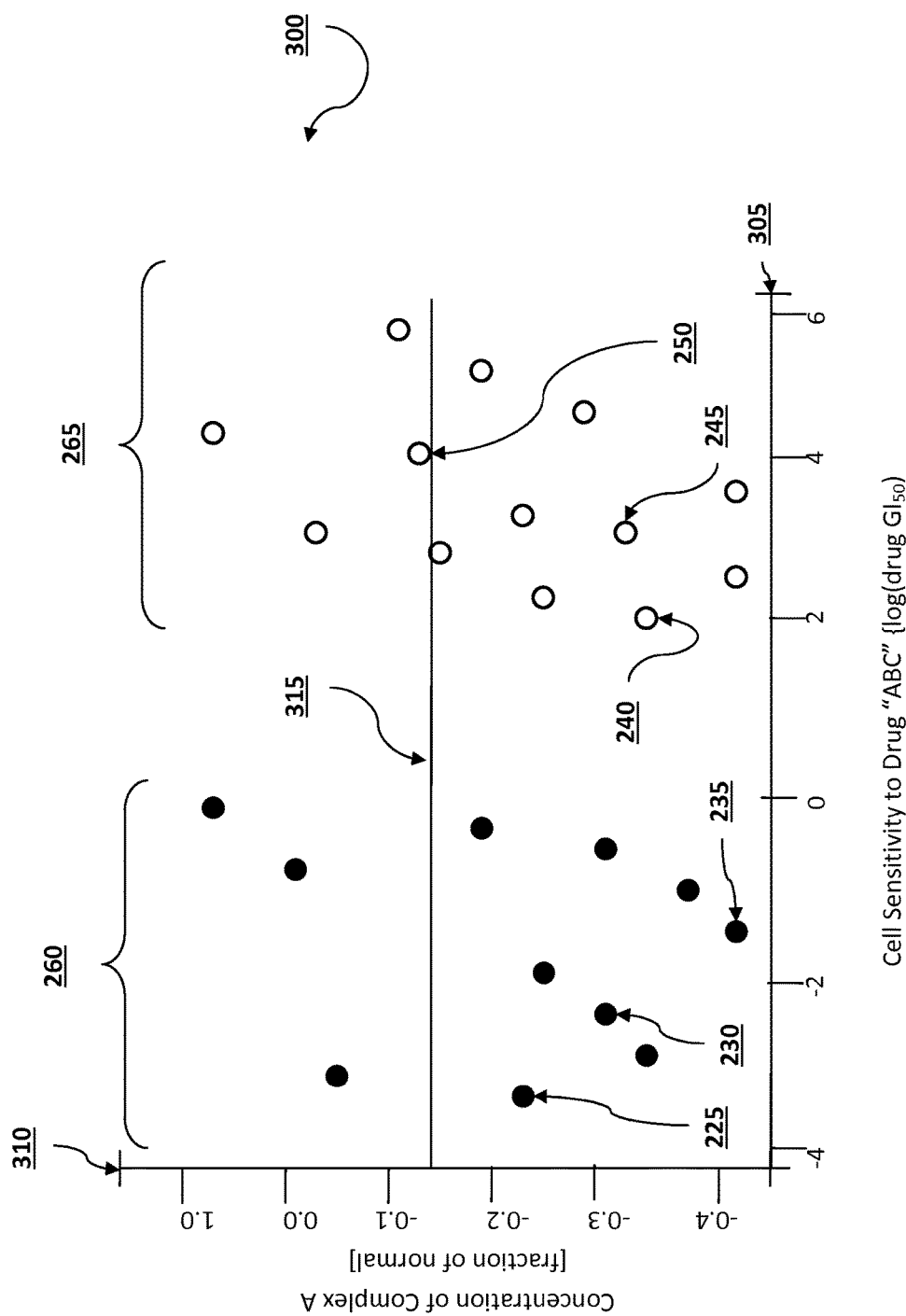
FIG. 3 depicts a graph illustrating the relationship between sensitivity levels of the cell lines and the magnitude of a measured expression present in the cell lines.

For example, FIG. 3 depicts graph 300 that shows the correlation between the expression (concentration of complex A) and the treatment effectiveness data 136. Axis 305 is similar to axis 205 of graph 200, which represents the treatment effective values (expressed in the $\log_{10}$ units of nanomolar drug concentrations for the $GI_{50}$ value for the drug NANT3456). Axis 310 represents magnitudes of an expression, and in this example, magnitudes of the expression: concentration of Complex A, from low magnitude (at the bottom of axis 310) to high magnitude (at the top of the axis 310). The values along axis 310 are expressed in terms of a fraction of normal concentration of the expression. Similar to graph 200, each data point in the graph 300 represents a different cell line. For example, data point 225 can represent cell line MV411, data point 230 can represent cell line TT, data point 235 can represent cell line PC3, data point 240 can represent NCIH23, data point 245 can represent cell line HT29, data point 250 can represent cell line CAPAN1, and so forth.

Figure 4:
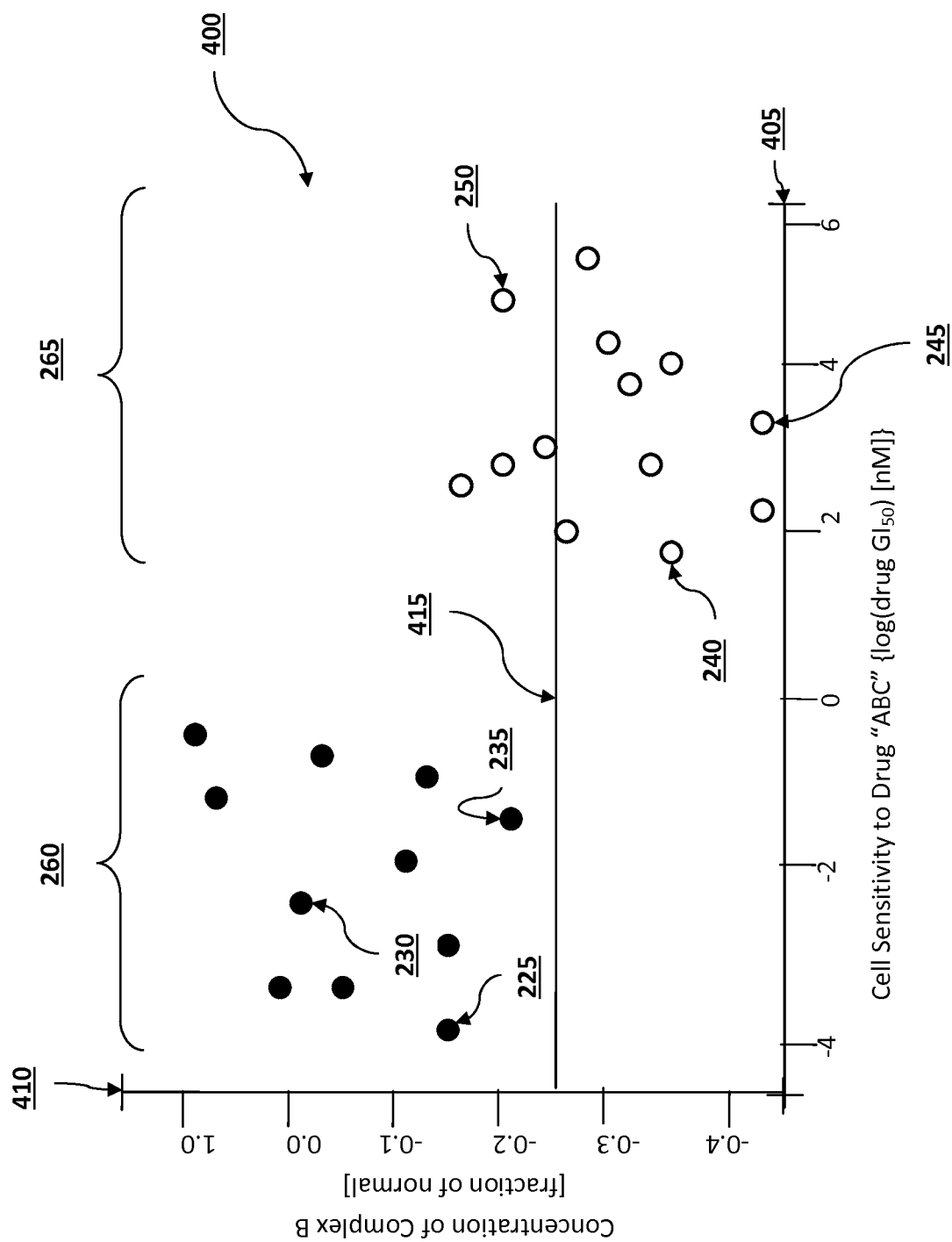
FIG. 4 depicts a graph illustrating the relationship between sensitivity levels of the cell lines and the magnitude of another measured expression present in the cell lines.
Figure 5:
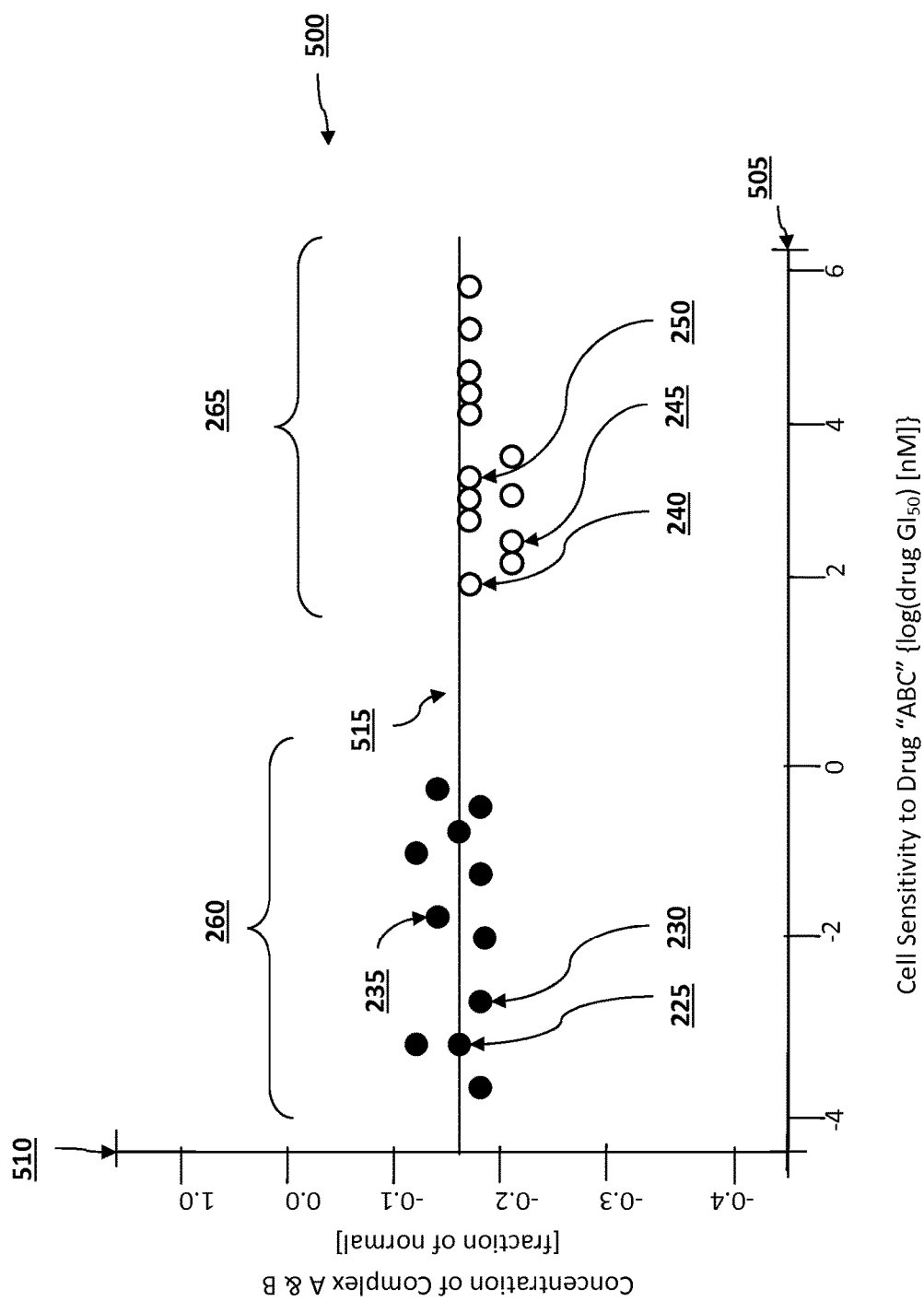
FIG. 5 depicts a graph illustrating the relationship between sensitivity levels of the cell lines and the magnitude of yet another measured expression present in the cell lines.
Figure 6:
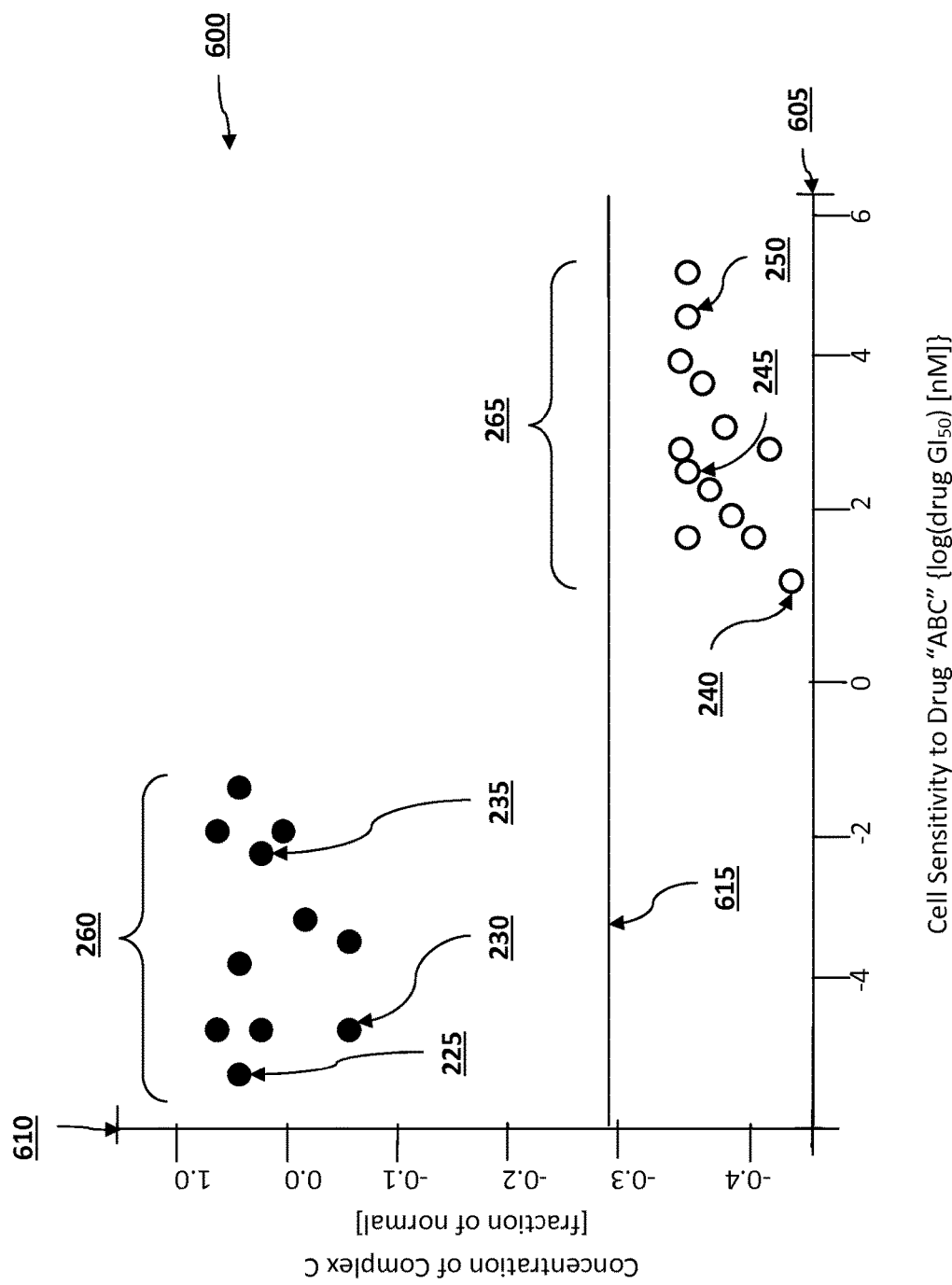
FIG. 6 depicts a graph illustrating the relationship between sensitivity levels of the cell lines and the magnitude of yet another measured expression present in the cell lines.

Similarly, FIG. 4 depicts graph 400 that shows the correlation between a different expression (concentration of Complex B) and the treatment effectiveness data 136, FIG. 5 depicts graph 500 that shows the correlation between a different expression (concentration of Complexes A and B) and the treatment effectiveness data 136, and FIG. 6 depicts graph 500 that shows the correlation between yet another expression (concentration of Complex C) and the treatment effectiveness data 136. As shown from FIGS. 3 through 6, the correlations between different expressions and the treatment effectiveness of the drug NANT 3456 can vary. In some embodiments, correlation module 140 sends all of this correlation data to marker determination module 150 for further analysis. Although correlations for only four different expressions are shown here, it has been contemplated that correlation module 140 can generate more correlation graphs for all possible expressions (different complexes, all permutations of combinations of complexes, etc.).

As mentioned above, marker determination module 150 is programmed to select an expression, out of all the possible expressions, with the most desirable (e.g., the best fit) correlation based on the correlation data received from correlation module 140, and determine a threshold expression magnitude value that a patient should exhibit in order to recommend administering the drug/treatment. In some embodiments, determination module 150 first finds a threshold expression magnitude value that optimally separates the sensitive cell lines (group 260 from FIG. 2) and the resistant cell lines (group 265 from FIG. 2) for all of the correlations generated by correlation module 140 and assigns a confidence score to that correlation based on how well the threshold expression magnitude value separates the two groups of cell lines. For example, if there is one magnitude value that can properly separate the two groups of cell lines on either side of the value (e.g., all sensitive cell lines have expression magnitudes that are above the value and all resistant cell lines have expression magnitudes that are below the value, or vice versa), then marker determination module 150 selects that value as the threshold expression value. If there is a range of magnitude values that can properly separate the two groups of cell lines on either side of the values (e.g., all sensitive cell lines have expression magnitudes that are above the values and all resistant cell lines have expression magnitudes that are below the values, or vice versa), then marker determination module 150 selects any one of the values (e.g., the median value). Because the threshold expression magnitude value can completely separate the two groups of cell lines in the above scenarios, marker determination module 150 would assign a 100% confidence score for each of the above correlations.

On the other hand, if no such magnitude exists, marker determination module 150 selects a magnitude value that separates the most number of cell lines (e.g., that causes as few cell lines to appear on the wrong side of the graph with respect to the threshold magnitude value) as possible. In these scenarios, marker determination module 150 reduces the confidence score by the percentage of cell lines that appear on the wrong side of the graph.

Applying the steps described above to correlation graph 300, marker determination module 150 would select magnitude value −0.18 (as shown by threshold 315) as the threshold value because it causes the least number of cell lines to appear on the "wrong" side of the graph. As shown in FIG. 3, three black data points (from group 260) and eight white data points (from group 265) out of a total of twenty-four (24) data points are on the wrong side of the threshold value. Consequently, there is a risk of false positives by the use of the complex with that threshold value (e.g., the threshold value based on the complex may indicate a patient as resistant when the patient is sensitive). Thus, marker determination module 150 assigns a confidence score of 13/24 (54%). It is noted that even though some of the expressions have a proportional relationship with the treatment effectiveness data. However, some other expressions, such as the one shown in FIG. 3 (concentration of Complex A) can have an inverse relationship with the treatment effectiveness data. That is, the less concentration of Complex A found in the cell implies a more effective result from the treatment of NANT3456. In this embodiment, marker determination module 150 also identifies a minimum diagnostically relevant value for the concentration of the expression (e.g., Complex A) due to the error rate of measuring concentration of the expression in a patient's sample cell.

Similarly, for graph 400, marker determination module 150 selects a threshold magnitude value of −0.25, as shown by threshold 415 in FIG. 4, and assigns a confidence score of 20/24 (83%). The correlation shown in graph 400 shows a proportional relationship between the expression and the treatment effectiveness value. For graph 500, marker determination module 150 selects a threshold magnitude value of −0.16, as shown by threshold 515 in FIG. 5, and assigns a confidence score of 20/24 (83%). The correlation shown in graph 500 shows an inverse relationship between the expression and the treatment effectiveness value. For graph 600, marker determination module 150 selects a threshold magnitude value of −0.29, as shown by threshold 615 in FIG. 6, and assigns a confidence score of 24/24 (100%). The correlation shown in graph 600 shows a proportional relationship between the expression and the treatment effectiveness value.

Based on the confidence scores of the different correlation graphs, marker determination module 150 determines that the expression for graph 600 (concentration of Complex C) has the most desirable correlation with the treatment effectiveness data as it has the highest (100%) confidence score. The threshold magnitude value for graph 600 (a concentration of Complex C of −0.29) is also used as part of the diagnostic test for determining whether the drug NANT3456 is suitable for a patient. In some embodiments, the machine learning system 100 also presents (displays) the diagnostic test (including the most desirable correlation graph such as graph 600 in this example and the threshold expression magnitude) to a user (via an output display device such as user terminal 138).

For any patient who has one of the diseases that the drug NANT3456 is designed to cure, one can take a sample diseased cell from the patient and obtain a magnitude value for Complex C (e.g., measure the concentration of Complex C in the sample diseased cell). According to the diagnostic test, patients whose sample cells have a concentration of Complex C that is higher than −0.29, as a fraction of the normal concentration, are recommended to use the treatment (e.g., take the drug NANT3456) and patients whose sample cells have a concentration of Complex C that is lower than −0.29 of the normal concentration are recommended not to use the treatment (e.g., take the drug NANT3456).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a patient having a tumor, the method comprising:
   inferring a plurality of protein expression magnitudes of known pathway elements from genomic and transcriptomic data from a plurality of data sets for a respective plurality of diseased cell lines, wherein each of the data sets comprises (a) genomics data and transcriptomics data for a plurality of known pathway elements and (b) quantitative responsiveness metric with respect to an action of a drug, and wherein the pathway elements are members of a pathway model;
   identifying from the plurality of data sets one set of correlation data among a plurality sets of correlation data based on a quality of correlation, wherein each set of correlation data corresponds to a plurality of correlations, each correlation between an expression magnitude of one of the known pathway elements and the quantitative responsiveness metric of a diseased cell line;
   identifying a threshold expression magnitude of one of the known pathway elements that qualitatively separates the plurality of correlations of the identified set of correlation data into a first set and a second set; and
   administering the drug to the patient, wherein a tumor sample taken from the patient exhibits mRNA expression of the pathway element that is higher than the threshold expression magnitude, and wherein the drug has the structure

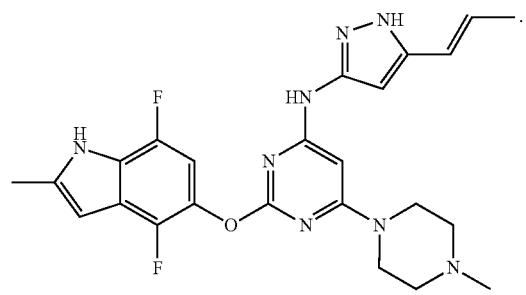 [SMILES: C/C=C/c1cc(Nc2cc(N3CCN(C)CC3)nc(Oc3cc(F)c4[nH]c(C)cc4c3F)n2)n[nH]1]

2. The method of claim 1, wherein the quantitative responsiveness metric comprises GI50 values or IC50 values.

3. The method of claim 1, wherein the first and second sets correspond to distinct members among the distinct diseased cell lines.

4. The method of claim 1, wherein determining the plurality of correlations, for each correlation, comprises generating data points in a graph that indicate expression magnitude of one of the known pathway elements in relation to the quantitative responsiveness metric of each distinct diseased cell line.

5. The method of claim 1, wherein the threshold expression magnitude is determined by assigning a confidence score to the correlation based on how well the first and second sets are separated.

6. The method of claim 5, wherein the confidence value is determined by a quantitative responsiveness metric of the distinct diseased cell lines located above or below the threshold expression magnitude.

7. The method of claim 1, wherein the protein expression magnitude is defined by at least a concentration of a complex.

8. The method of claim 1, wherein the protein expression magnitude is defined by at least a concentration of a combination of multiple complexes.

9. The method of claim 1, wherein the protein expression magnitude is defined at least by a ratio of concentration between two or more complexes.

10. The method of claim 1, further comprising generating a known quantitative responsiveness by testing example diseased cells of the plurality of distinct diseased cell lines with the drug.

11. The method of claim 1, wherein a first set of correlation corresponds to a first subset of plurality of distinct cell lines that are sensitive to treatment with the drug, and wherein a second set of correlation corresponds to a second subset of plurality of distinct cell lines that are resistant to treatment with the drug.

12. The method of claim 1, wherein the genomics data and transcriptomics data are selected from the group consisting of gene copy number data, gene mutation data, gene methylation data, gene expression data, RNA splice information data, siRNA data, and RNA translation data.

* * * * *